US008884187B2

(12) United States Patent
Nakatate et al.

(10) Patent No.: US 8,884,187 B2
(45) Date of Patent: Nov. 11, 2014

(54) WELDING OBSERVATION APPARATUS

(75) Inventors: Kenichi Nakatate, Sakura (JP); Takashi Tsumanuma, Sakura (JP); Satoshi Katou, Hitachi (JP); Akemi Katou, legal representative, Hitachi (JP); Jun Yamagishi, Tokyo (JP)

(73) Assignee: Fujikura Ltd., Tokyo (JP)

( * ) Notice: Subject to any disclaimer, the term of this patent is extended or adjusted under 35 U.S.C. 154(b) by 1265 days.

(21) Appl. No.: 12/596,045

(22) PCT Filed: Apr. 11, 2008

(86) PCT No.: PCT/JP2008/057193
§ 371 (c)(1),
(2), (4) Date: Apr. 26, 2010

(87) PCT Pub. No.: WO2008/133053
PCT Pub. Date: Nov. 6, 2008

(65) Prior Publication Data
US 2010/0206851 A1    Aug. 19, 2010

(30) Foreign Application Priority Data

Apr. 16, 2007    (JP) ................................. 2007-106651

(51) Int. Cl.
*B23K 9/10*    (2006.01)
*G02B 5/20*    (2006.01)
(Continued)

(52) U.S. Cl.
CPC ................. *B23K 9/0956* (2013.01); *G02B 5/23* (2013.01); *G02B 5/208* (2013.01);
(Continued)

(58) Field of Classification Search
CPC ............................ B29D 11/00432; G02C 7/02

USPC ...................... 219/130.01, 124.34; 901/42, 47
See application file for complete search history.

(56) References Cited

U.S. PATENT DOCUMENTS 4,859,829 A * 8/1989 Dufour .................... 219/124.34
(Continued)

FOREIGN PATENT DOCUMENTS

CN         1248698 A     3/2000
CN         1448239 A     10/2003
(Continued)

OTHER PUBLICATIONS

Office Action issued by Japanese Patent Office in Japanese Patent Application No. 2007-106651 dated Feb. 5, 2013.
(Continued)

*Primary Examiner* — S. V. Clark
*Assistant Examiner* — Ali Naraghi
(74) *Attorney, Agent, or Firm* — Sughrue Mion, PLLC

(57) ABSTRACT

A welding observation apparatus is provided to use partial darkening by a telecentric optical system and a photochromic filter (PCF) as an optical system for filtering light emission from arc discharge in order to verify the welding condition under the welding arc discharge, without forming an image on the PCF, so that light reducing performance can be secured even if a focus shifts from on the PCF, with satisfactory monitoring of welding condition.
The welding observation apparatus comprises: an arc welding unit 8; an objective optical system (1, 2) for concentrating light from the arc welding unit 8; a telecentric optical system 3 for guiding the light concentrated by the objective optical system (1, 2); a PCF 4 for illuminating with the light guided by the telecentric optical system 3; and a solid state imaging device 9 for receiving the light passing through the PCF 4, wherein the light from the arc welding unit 8 is partial-darkened by the PCF 4.

18 Claims, 13 Drawing Sheets

(51) Int. Cl.
*G02B 13/22* (2006.01)
*B23K 31/12* (2006.01)
*B23K 9/095* (2006.01)
*B23K 9/32* (2006.01)
*G01N 21/67* (2006.01)
*G02B 5/23* (2006.01)

(52) U.S. Cl.
CPC ............. *G02B 13/22* (2013.01); *B23K 31/125* (2013.01); *B23K 9/321* (2013.01); *G01N 21/67* (2013.01); *Y10S 901/42* (2013.01)
USPC ........................... 219/130.01; 124/34; 901/42

(56) References Cited

U.S. PATENT DOCUMENTS 5,255,088 A * 10/1993 Thompson ...................... 348/90
5,353,080 A * 10/1994 Christman .................... 396/355
6,392,184 B1 * 5/2002 Yokota et al. ................... 219/74

FOREIGN PATENT DOCUMENTS

| | | | |
|---|---|---|---|
| CN | 1786753 | A | 6/2006 |
| CN | 1844891 | A | 10/2006 |
| JP | 52-129537 | A | 10/1977 |
| JP | 52129537 | A * | 10/1977 |
| JP | 62-032417 | A | 2/1987 |
| JP | 62032417 | A * | 2/1987 |
| JP | 09-024470 | A | 1/1997 |
| JP | 3140275 | B2 * | 3/2001 |
| JP | 2002-316279 | A | 10/2002 |
| JP | 2005-262224 | A | 9/2005 |

OTHER PUBLICATIONS

Japanese Office Action dated May 22, 2012 issued in counterpart Japanese Application No. 2007-106651.
Communication from the Korean Patent Office dated May 24, 2011 in a counterpart application 10-2009-7023850.
Communication from the Chinese Patent Office in Chinese Application No. 200880012428.0 dated May 16, 2012.
Notification of Submission of Arguments issued Nov. 11, 2011 by the Korean Intellectual Property Office in counterpart Korean Patent Application No. 10-2009-7023850.

* cited by examiner

WELDING OBSERVATION APPARATUS

CROSS REFERENCE TO RELATED APPLICATIONS

This application is a National Stage of International Application No. PCT/JP2008/057193 filed Apr. 11, 2008, claiming priority based on Japanese Patent Application No. 2007-106651 filed Apr. 16, 2007, the contents of all of which are incorporated herein by reference in their entirety.

TECHNICAL FIELD

The present invention relates to a welding observation apparatus, and in particular, relates to a welding observation apparatus having the characteristic in an optical system for filtering light emission from arc discharge in order to verify a welding condition under a welding arc discharge.

BACKGROUND ART

There are a TIG (Tungsten Inert Gas Welding) method, a MIG (Metal Inert Gas Welding) method, a MAG (Metal Active Gas Welding) method, etc. in arc welding, for example. Moreover, there area $CO_2$ gas arc welding method (MAG) etc.

The TIG method is a method of generating an arc between a tungsten electrode and a base material in the inert gas atmosphere, such as argon or a helium, and welding by melting a base material and a wedding rod (or welding filler rod) using this arc heat. The tungsten electrode only generates the arc, and does not perform melting shift itself.

In the MAG method, when the welding is started, a welding wire is provided continuously, the arc generated between the welding wire and the base material is continued, and then the welding proceeds. The welding wire is an electrode for generating the arc, and also is melted itself and forms a welding metal with the generated arc heat. In this case, although the welding metal is covered and the atmospheric bad influence is prevented with the shielding gas which flows out from a nozzle of a welding torch tip region, $CO_2$ gas, gaseous argon, and gas which mixes the gaseous argon to the $CO_2$ gas, etc. are used as the shielding gas. The term of the MAG welding is defined in consideration of the kind and characteristics of shielding gas, and the principle as the welding method is the same as the MIG welding or the $CO_2$ gas arc welding.

Although the principle of the MIG method is the same as the MAG method, the gas using inert gas (inactive gas), such as argon and a helium (or these mixed gas), or performed light doping of active gas (activated gas), such as $CO_2$ gas and oxygen, to the inert gas is used as the kind of shielding gas.

Since the arc of the arc welding generally emits a strong light, in particular ultraviolet radiation and visible light, much keratitis and conjunctivitis have been occurred by the ultraviolet radiation in the shop floor. Moreover, an example of retinopathy by visible light is also reported. Although a welding arc emits light to wide wavelength range of ultra-violet, visible, and infrared simultaneously, generally the shape of its spectrum changes with a welding method or conditions.

Also in each the method of the TIG method, the MIG method, and the MAG method, in a conventional welding observation apparatus, there is a problem that an optical dynamic range is narrow and it is difficult to observe simultaneously between the high luminance part of weld and the dark parts of the peripheral part of weld, at the time of the welding.

In a conventional welding observation apparatus using an electronic image synthesis etc. in order to solve the above-mentioned problem, the apparatus becomes large and complicated, is hard to be attached, and is expensive.

In a conventional welding observation apparatus using high-luminance lighting in order to solve the above-mentioned problem, such as laser illumination, the apparatus is large, is hard to be attached, and is expensive, and there is a problem that the arc part is unobservable since it cannot colorize with laser illumination.

In a conventional welding observation apparatus using an ND (Neutral Density) filter in order to solve the above-mentioned problem, there is a problem that the dark part of the peripheral part of weld is unobservable since the color image cannot obtain vividly.

In a conventional welding observation apparatus using a partial filter in order to solve the above-mentioned problem, it is necessary to fix the position for disposing the partial filter on screen constitution.

It is already disclosed in FIG. 2 of Patent Literature 1 about an apparatus and a method for performing video observation of the arc welding.

Patent Literature 1: Specification of U.S. Pat. No. 5,255,088

A lens constitution and a system for filtering various lights generated under the arc welding environment are disclosed in Patent Literature 1. In the system according to Patent Literature 1, the contrast of the high-luminance light of the weld generated at the time of arc welding is reduced dramatically, and the suitable remote monitor is made possible. More specifically, the negative image of the arc welding part is formed by using a photochromic lens. In the system according to Patent Literature 1, the negative image of the arc welding unit formed using the photochromic lens functions as a density variable optical filter for reducing the luminance of the weld which illuminates on the photochromic lens and is formed an image. In the system according to Patent Literature 1, first of all, the light of the arc welding part is made to concentrate and form an image on the photochromic lens using a first lens, and next, the ultraviolet light is removed by using a second lens and the image input into a camera is formed.

In the system of above-mentioned Patent Literature 1 using the photochromic lens, there is a problem that a highly efficient PCF (Photochromic Filter) is needed, and also the light reducing performance is reduced rapidly when a focus shifts.

The purpose of the present invention is to provide a welding observation apparatus using partial darkening by a telecentric optical system and a PCF as an optical system for filtering light emission from arc discharge in order to verify the welding condition under the welding arc discharge, without forming an image on the PCF, so that light reducing performance can be secured even if a focus shifts from on the PCF, with satisfactory monitoring of welding condition.

DISCLOSURE OF INVENTION

According to one aspect of the present invention, it is provided of a welding observation apparatus comprising: an arc welding unit; an objective optical system for concentrating light from the arc welding unit; a telecentric optical system for guiding the light concentrated by the objective optical system; a photochromic filter for illuminating with the light guided by the telecentric optical system; and a solid state imaging device for receiving the light passing through the photochromic filter, wherein the light from the arc welding unit is partial-darkened by the photochromic filter.

According to another aspect of the present invention, it is provided of a welding observation apparatus comprising: an arc welding unit; an objective optical system including a window unit for concentrating light from the arc welding unit, and a first colour filter for illuminating with the light concentrated by the window unit; a telecentric optical system for guiding the light passing through the first colour filter; second and third colour filters for illuminating with the light guided by the telecentric optical system; and a solid state imaging device for receiving the light passing through the second and third colour filters, wherein the light from the arc welding unit is partial-darkened by the third colour filter.

According to another aspect of the present invention, it is provided of a welding observation apparatus comprising: an arc welding unit; an objective optical system including a window unit for concentrating light from the arc welding unit, and a first colour filter for illuminating with the light concentrated by the window unit; a telecentric optical system for guiding the light passing through the first colour filter; a photochromic filter for illuminating with the light guided by the telecentric optical system; second and third colour filters for illuminating with the light passing through the photochromic filter; and a solid state imaging device for receiving the light passing through the second and third colour filters, wherein the light from the arc welding unit is partial-darkened by the third colour filter and the photochromic filter.

According to another aspect of the present invention, it is provided of a welding observation apparatus comprising: an arc welding unit; an objective optical system for concentrating light from the arc welding unit; an image fiber for guiding the light concentrated by the objective optical system; and a camera unit including a photochromic filter for illuminating with the light guided by the image fiber, and a solid state imaging device for receiving the light passing through the photochromic filter, wherein the light from the arc welding unit is partial-darkened by the photochromic filter.

According to another aspect of the present invention, it is provided of a welding observation apparatus comprising: an arc welding unit; an objective optical system including a window unit for concentrating light from the arc welding unit, and a first colour filter for illuminating with the light concentrated by the window unit; an image fiber for guiding the light passing through the first colour filter; a camera unit including second and third colour filters for illuminating with the light guided by the image fiber, and a solid state imaging device for receiving the light passing through the second and third colour filters, wherein the light from the arc welding unit is partial-darkened by the third colour filter.

According to another aspect of the present invention, it is provided of a welding observation apparatus comprising: an arc welding unit; an objective optical system including a window unit for concentrating light from the arc welding unit, and a first colour filter for illuminating with the light concentrated by the window unit; an image fiber for guiding the light passing through the first colour filter; and a camera unit including a photochromic filter for illuminating with the light guided by the image fiber, second and third colour filters for illuminating with the light passing through the photochromic filter, and a solid state imaging device for receiving the light passing through the second and third colour filters, wherein the light from the arc welding unit is partial-darkened by the third colour filter and the photochromic filter.

BEST MODE FOR CARRYING OUT THE INVENTION

Figure 1:
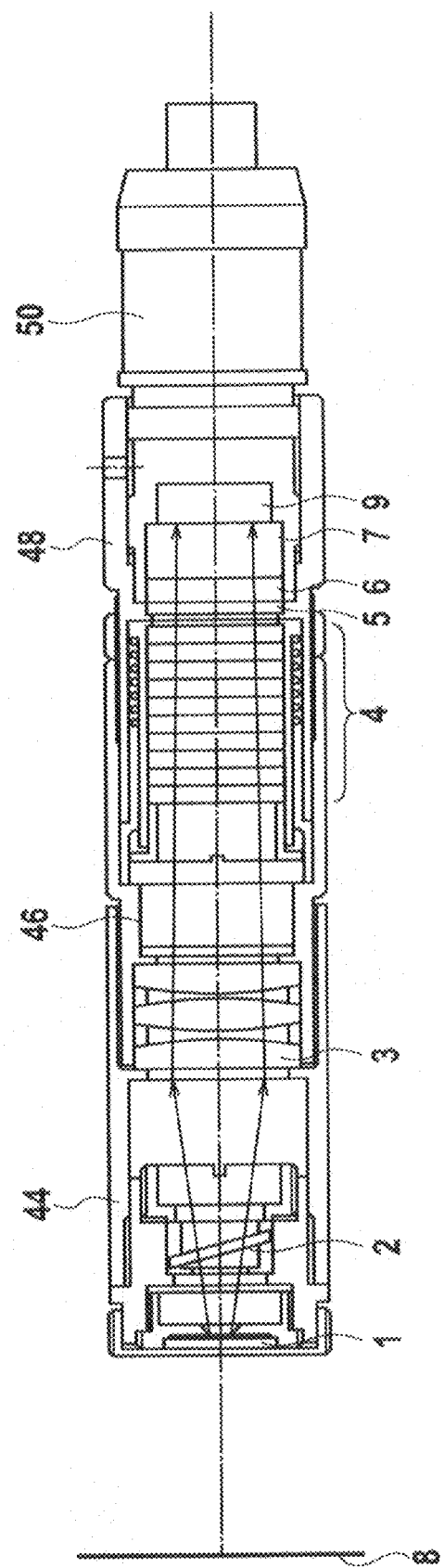
FIG. 1 It is a schematic cross-sectional configuration chart of a welding observation apparatus according to a first embodiment of the present invention.

Next, an embodiment of the invention is described with reference to drawings. In the description of the following drawings, the identical or similar reference numeral is attached to the identical or similar part. However, a drawing is schematic and it should care about differing from an actual thing. Of course, the part from which the relation and ratio of a mutual size differ also in mutually drawings is included.

The embodiment shown in the following exemplifies the device and method for materializing the technical idea of the present invention, and the technical idea of the present invention does not specify placement of each component parts, etc. as the following. The technical idea of the present invention can add various change in scope of claims.

First Embodiment

Figure 2:
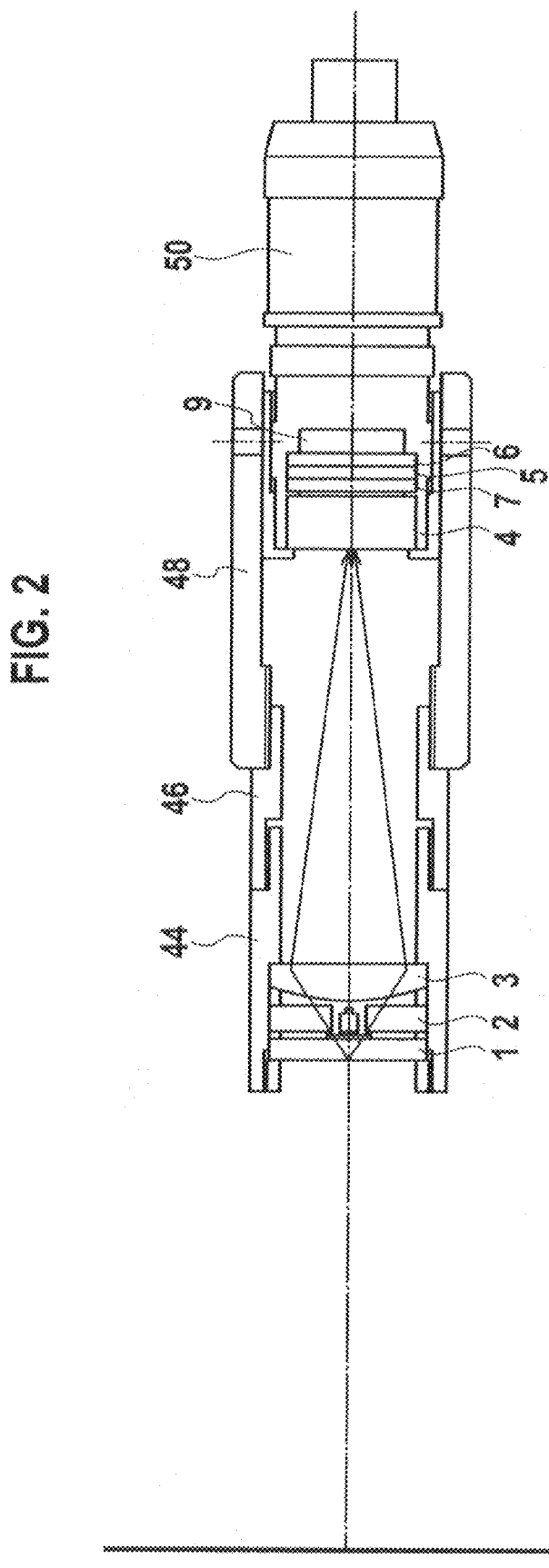
FIG. 2 It is a schematic cross-sectional configuration chart of a welding observation apparatus according to a comparative example of the first embodiment of the present invention.

FIG. 1 shows a schematic cross-section structure of a welding observation apparatus according to a first embodiment of the present invention. Moreover, FIG. 2 shows a schematic cross-section structure of a welding observation apparatus according to a comparative example of the first embodiment of the present invention.

As shown in FIG. 1, the welding observation apparatus according to the first embodiment of the present invention includes: an arc welding unit 8; an objective optical system (1) for concentrating the light from the arc welding unit 8; a telecentric optical system (3) for guiding the light concentrated by the objective optical system (1); a PCF 4 for illuminating with the light guided by the telecentric optical system (3); and a solid state imaging device 9 for receiving the light passing through the PCF 4. The PCF 4 partial-darkens the light from the arc welding unit 8.

Alternatively, as shown in FIG. 1, the welding observation apparatus according to the first embodiment of the present invention includes: an arc welding unit 8; an objective optical system including a window unit 1 for concentrating the light from the arc welding unit 8, and a first colour filter 2 for illuminating with the light concentrated by the window unit 1; a telecentric optical system (3) for guiding the light passing through the colour filter 2; second and third colour filters (5, 6) for illuminating with the light guided by the telecentric optical system (3); and a solid state imaging device 9 for receiving the light passing through the second and third colour filters (5, 6). The light from the arc welding unit 8 is partial-darkened by the third colour filter 6.

Alternatively, as shown in FIG. 1, the welding observation apparatus according to the first embodiment of the present invention includes: an arc welding unit 8; an objective optical system including the window unit 1 for concentrating the light from the arc welding unit 8, and a first colour filter 2 for illuminating with the light concentrated by the window unit 1; a telecentric optical system (3) for guiding the light passing through the colour filter 2; a PCF 4 for illuminating with the light guided by the telecentric optical system (3); second and third colour filters (5, 6) for illuminating with the light passing through the PCF 4; and a solid state imaging device for receiving the light passing through the second and third colour filters (5, 6). The light from the arc welding unit 8 is partial-darkened by the third colour filter 6 and the PCF 4.

In FIG. 1, the objective optical system includes the window unit 1, and is disposed in a spacer 44. The telecentric optical system includes an objective lens 3, and is housed in a lens holder 46. The reference numeral 48 denotes a body, the reference numeral 50 denotes a camera head, and the reference numeral 7 denotes a low pass filter.

As shown in FIG. 2, the welding observation apparatus according to the comparative example of the first embodiment of the present invention includes: an arc welding unit 8; an objective optical system provided with a window unit 1 for concentrating the light from the arc welding unit 8, and a first colour filter 2 for illuminating with the light concentrated by the window unit; an objective lens 3 for guiding the light passing through the colour filter 2; a PCF 4 in which the light guided by the objective lens 3 forms an images; second and third colour filters (5, 6) for illuminating with the light passing through the PCF 4; and a solid state imaging device 9 for receiving the light passing through the second and third colour filters (5, 6). The light from the arc welding unit 8 is partial-darkened by the third colour filter 6 and the PCF 4.

The telecentric optical system is not used in the welding observation apparatus according to the comparative example of the first embodiment of the present invention. Since the light guided by the objective lens 3 forms an image on the surface of the PCF 4, if highly efficient PCF 4 is used, it is possible to dim the light from the arc welding unit 8 by dramatic contrast. However, the light guided by the objective lens 3 forms an image on the surface of the PCF 4. Therefore, when the focus shifts if only a little, the dimming characteristics deteriorates rapidly since it is a configuration with the shallow depth of focus.

On the other hand, in the welding observation apparatus according to the first embodiment of the present invention, as shown in FIG. 1, the depth of focus becomes deep by using the telecentric optical system, and it cannot dim by dramatic contrast, but various advanced features of a colonization image being obtained, wide dynamic range characteristics being obtained, the partial darkening being possible by superimposing a plurality of PCFs of low cost, etc. are achievable.

Figure 3:
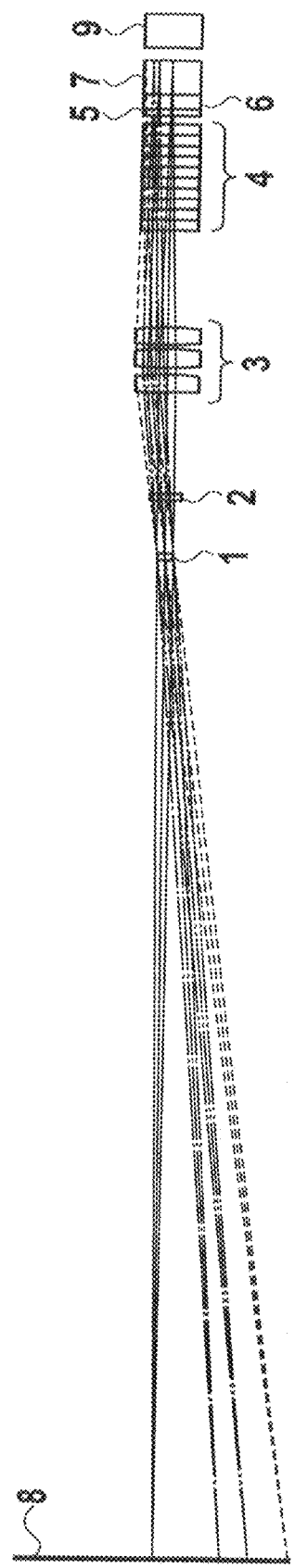
FIG. 3 It is an optical path diagram of the welding observation apparatus according to the first embodiment of the present invention.

FIG. 3 shows a schematic optical path diagram of the welding observation apparatus according to the first embodiment of the present invention. FIG. 3 corresponds to the welding observation apparatus according to the first embodiment of the present invention shown in FIG. 1.

The window unit 1 includes the function to calibrate a total amount of light. It can also be concluded that a part of telecentric optical system is composed with the objective lens 3.

Figure 4:
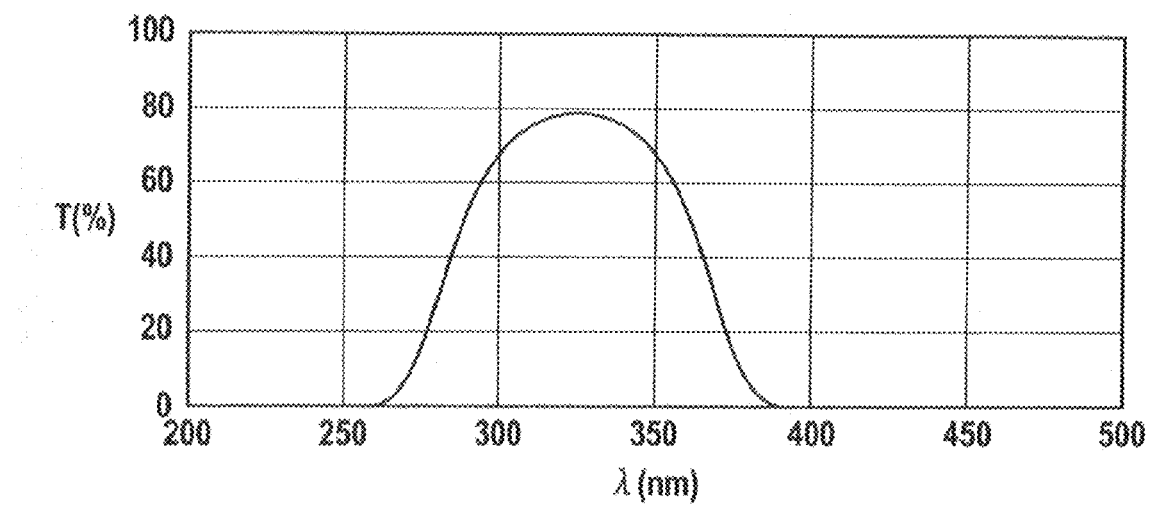
FIG. 4 It is an example of a filtering characteristic of a first colour filter applied to the welding observation apparatus according to the first embodiment of the present invention.
Figure 5:
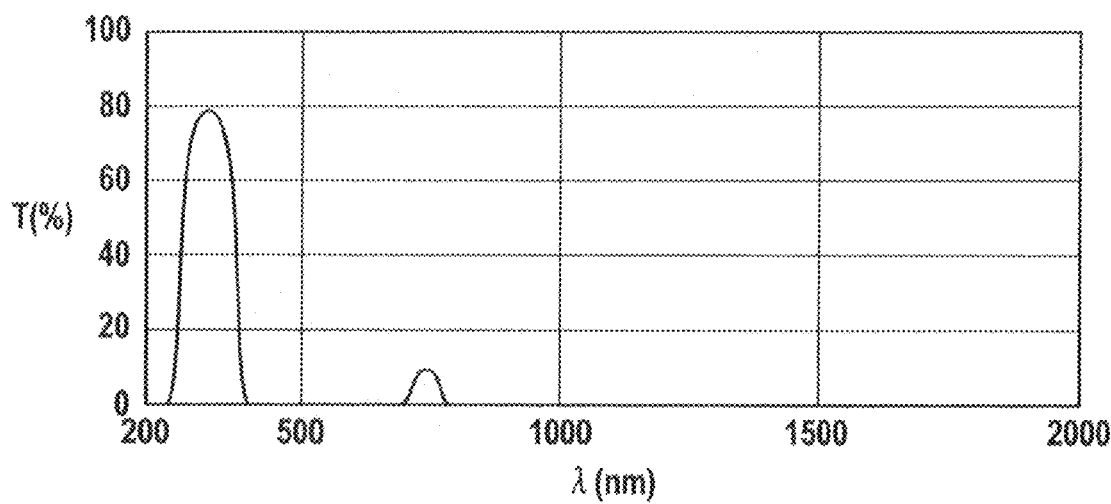
FIG. 5 It is an example of a filtering characteristic of the first colour filter applied to the welding observation apparatus according to the first embodiment of the present invention.

The first colour filter 2 has performance for passing through ultraviolet light (UV) and absorbing or reflecting visible light (VIS). FIG. 4 shows an example of the filtering characteristic of the first colour filter 2 (200 nm to 500 nm), and FIG. 5 shows an example of the filtering characteristic of the first colour filter 2 (200 nm to 2000 nm).

Although the objective lens 3 is a lens for image formation, both the UV light and the VIS light can be passed through.

The PCF 4 has performance for performing the concentration change partially by the UV light, and performing the mask of the VIS light.

Figure 6:
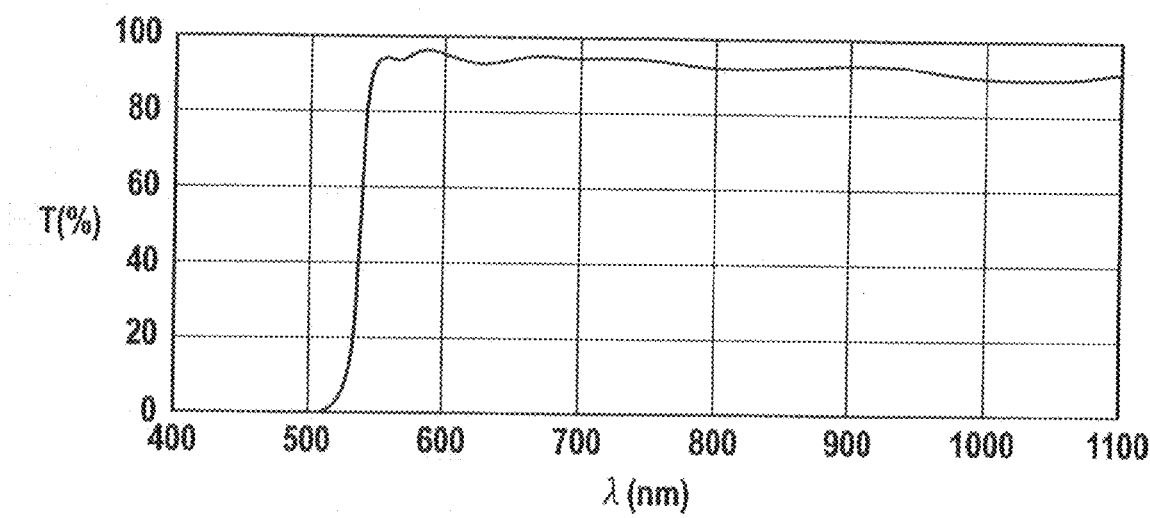
FIG. 6 It is an example of a filtering characteristic of a second colour filter applied to the welding observation apparatus according to the first embodiment of the present invention.

The second colour filter 5 has performance for reflecting the UV light and passing through the VIS light for protection of the solid state imaging device 9. FIG. 6 shows an example of the filtering characteristic of the second colour filter 5.

Figure 7:
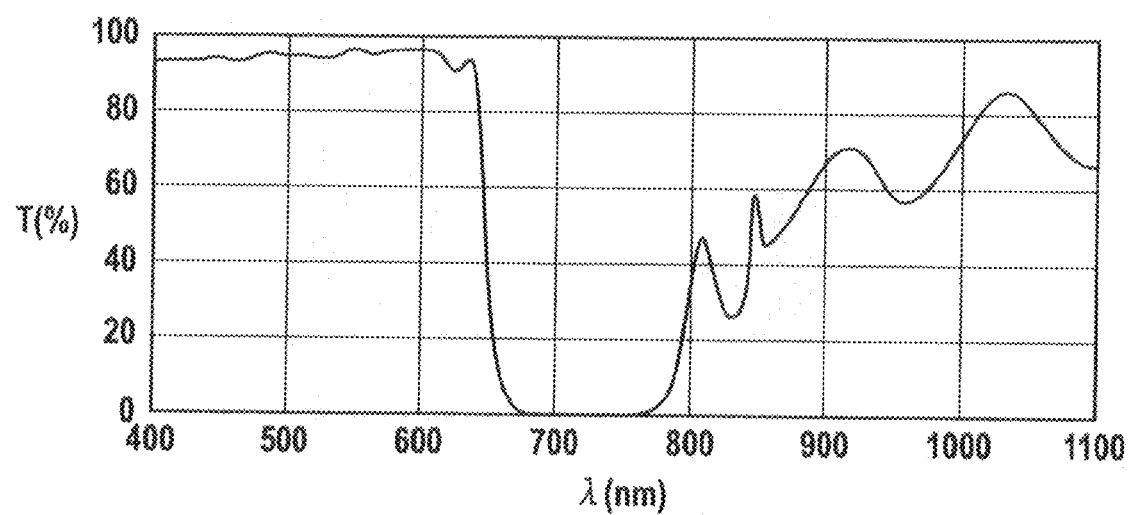
FIG. 7 It is an example of a filtering characteristic of a third colour filter applied to the welding observation apparatus according to the first embodiment of the present invention.

The third colour filter 6 has performance for reflecting the infrared (IR) light and passing through the VIS light. FIG. 7 shows an example of the filtering characteristic of the third colour filter 6. The third colour filter 6 is a filter for wavelength selection, and functions as a band pass filter having an optical window wavelength, for example, as shown in FIG. 7.

(Performance of CCD Camera)

Figure 8:
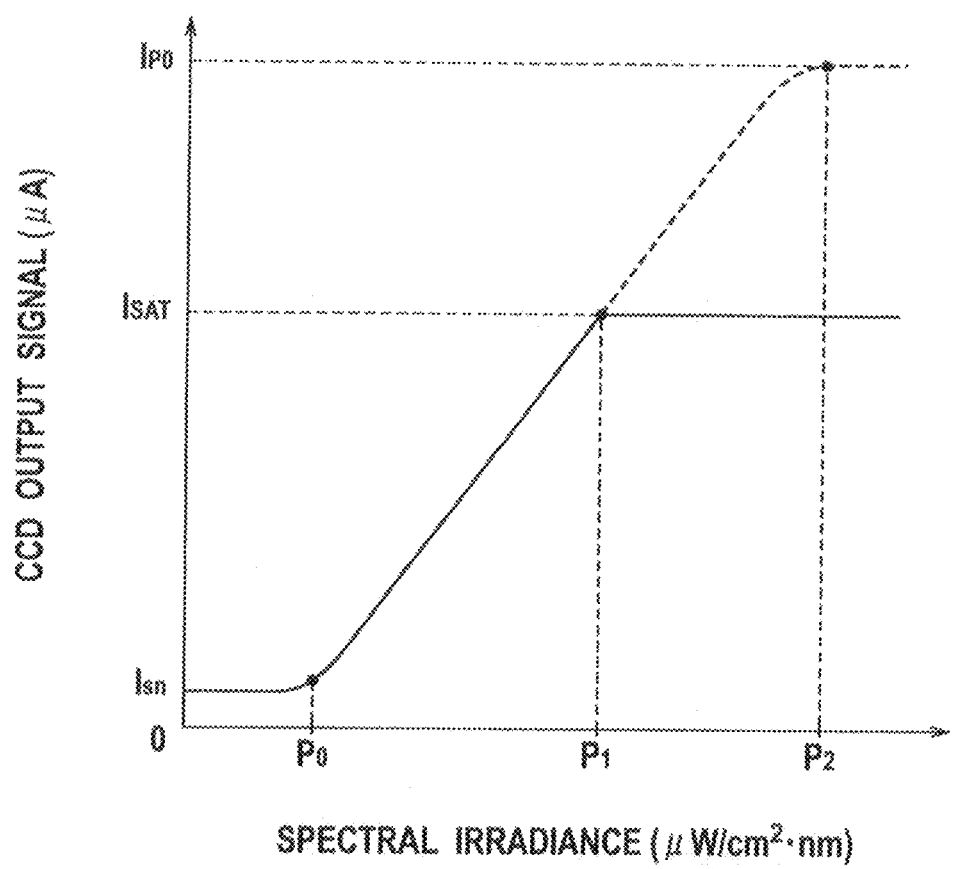
FIG. 8 It is a schematic diagram for explaining the relation between a CCD output signal and spectral irradiance of a solid state imaging device (CCD) applied to the welding observation apparatus according to the first embodiment of the present invention.

FIG. 8 is a schematic diagram for explaining the relation between the output signal and the spectral irradiance of CCD (Charge Coupled Device) as a solid state imaging device applied to the welding observation apparatus according to the first embodiment of the present invention.

Since the part of the arc is extremely bright in arc welding, such as TIG, MIG, and MAG, the dynamic range is insufficient in the usual CCD camera. Therefore, the arc and the work are simultaneously unobservable.

That is, as shown in FIG. 8, as for the CCD output signal, the substantially linear dynamic range is obtained in the range between a spectral irradiance $P_0$ decided by a dark current $I_{sn}$, and a spectral irradiance $P_1$ decided by a saturated output signal $I_{SAT}$.

The CCD output signal becomes the saturated output signal $I_{SAT}$ in the spectral irradiance $P_1$, and is fixed to the saturated output signal $I_{SAT}$ in the spectral irradiance $P_2$ greater than $P_1$, and it cannot obtain the output signal $I_{PO}$ expected in the wide dynamic range.

In the welding observation apparatus according to the first embodiment of the present invention, in order to keep up the colorization and the miniaturization of the camera, the filter named the PCF from which the concentration in the visible region changes with the ultraviolet rays is used. Since a plenty of ultraviolet rays are emitted from the arc part in the welding of TIG, MIG and MAG, it is made to dim in a visible light wavelength region by making the PCF black partially using the PCF.

The ultra-violet image is not made to form an image on the PCF in the welding observation apparatus according to the first embodiment of the present invention. The light ray flux of the ultraviolet light and the visible light does not spread in the whole PCF, but is passed through on a small scale partially, by using the telecentric optical system for a lens. Accordingly, although the contrast is not as sharp as the welding observation apparatus according to the comparative example of the first embodiment of the present invention, the part of strong light of ultraviolet light, i.e., the part of the arc, can be dimmed partially and spatially. Accordingly, even if the rate of the concentration change of PCF is low, the dimming characteristics can be strengthened by superimposing a plurality of PCFs. In the TIG welding, the satisfactory observation result is obtained, for example, a welding observation apparatus whose diameter of visual field is degree 40 mm and working distance (WD) is about 150 mm is obtained.

Although the welding arc emits the light to the wide wavelength range of ultra-violet, visible and infrared simultaneously, generally the shape of its spectrum changes with a welding method or conditions.

Figure 9:
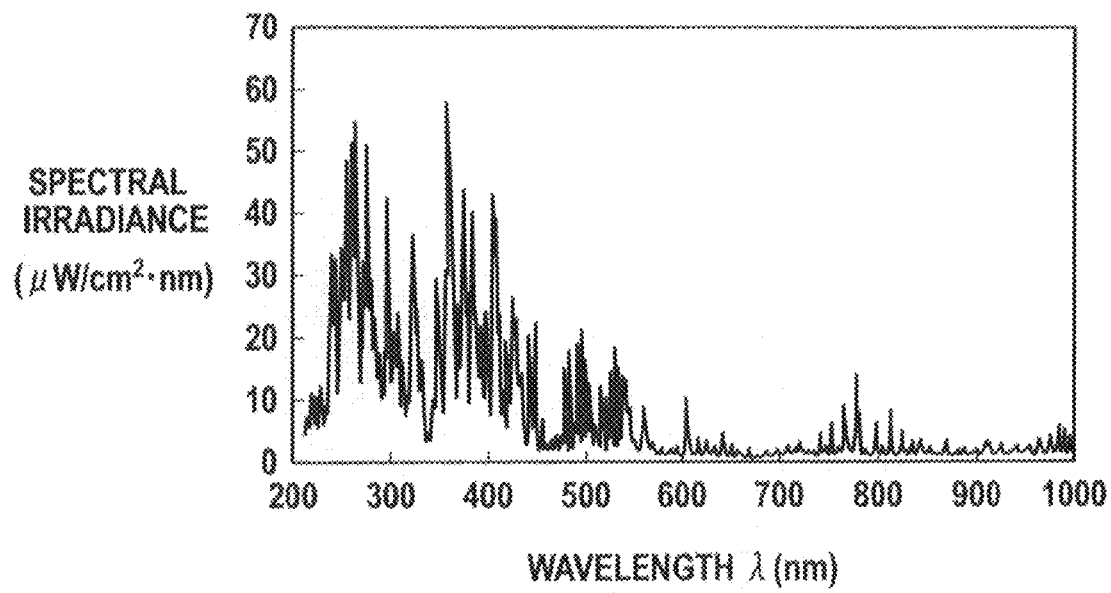
FIG. 9 It is an example showing the relation (luminescence spectrum) between the spectral irradiance and wavelength in MAG welding of soft steel.
Figure 10:
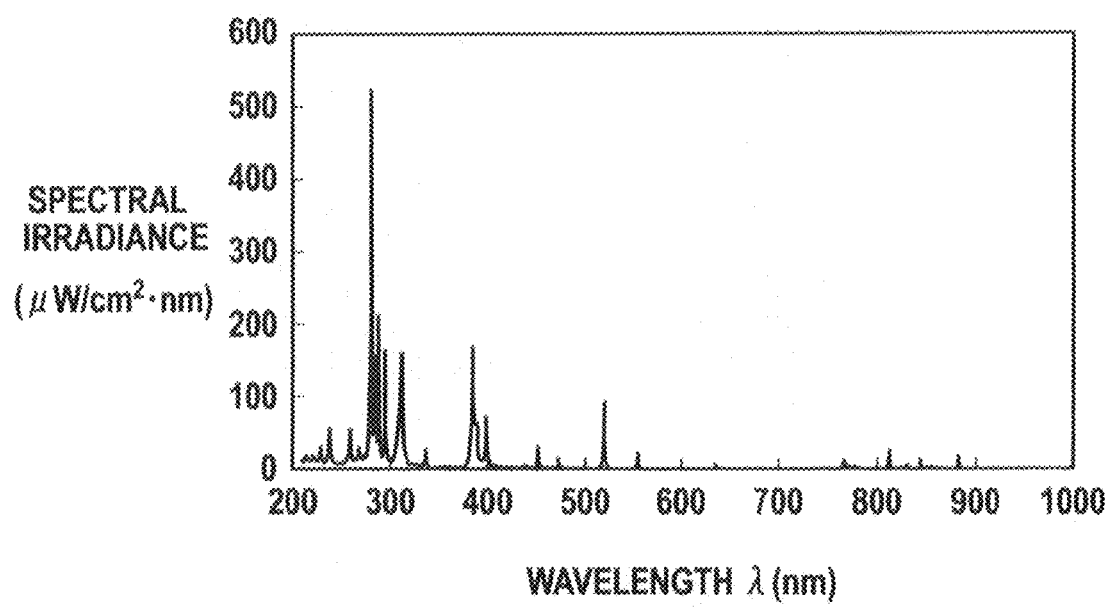
FIG. 10 It is an example showing the relation (luminescence spectrum) between the spectral irradiance and wavelength in MIG welding of an aluminum alloy.

An example of the spectrum (wavelength distribution) of the light to generate is shown in FIG. 9 and FIG. 10.

FIG. 9 shows an example showing the relation (luminescence spectrum) between the spectral irradiance and the wavelength in the MAG welding of soft steel, and shows the spectral irradiance in a position with a distance of about 1 meter from the arc. Most of the line spectra are in accordance with a ferrum (Fe), and, in the case of welding of soft steel and stainless steel, it becomes with the spectrum of the shape similar to this.

FIG. 10 shows an example showing the relation (luminescence spectrum) between the spectral irradiance and the wavelength in the MIG welding of an aluminum alloy, and shows the spectral irradiance in a position with a distance of about 1 meter from the arc. Most of the line spectra are in accordance with aluminum, magnesium, and argon.

Figure 11:
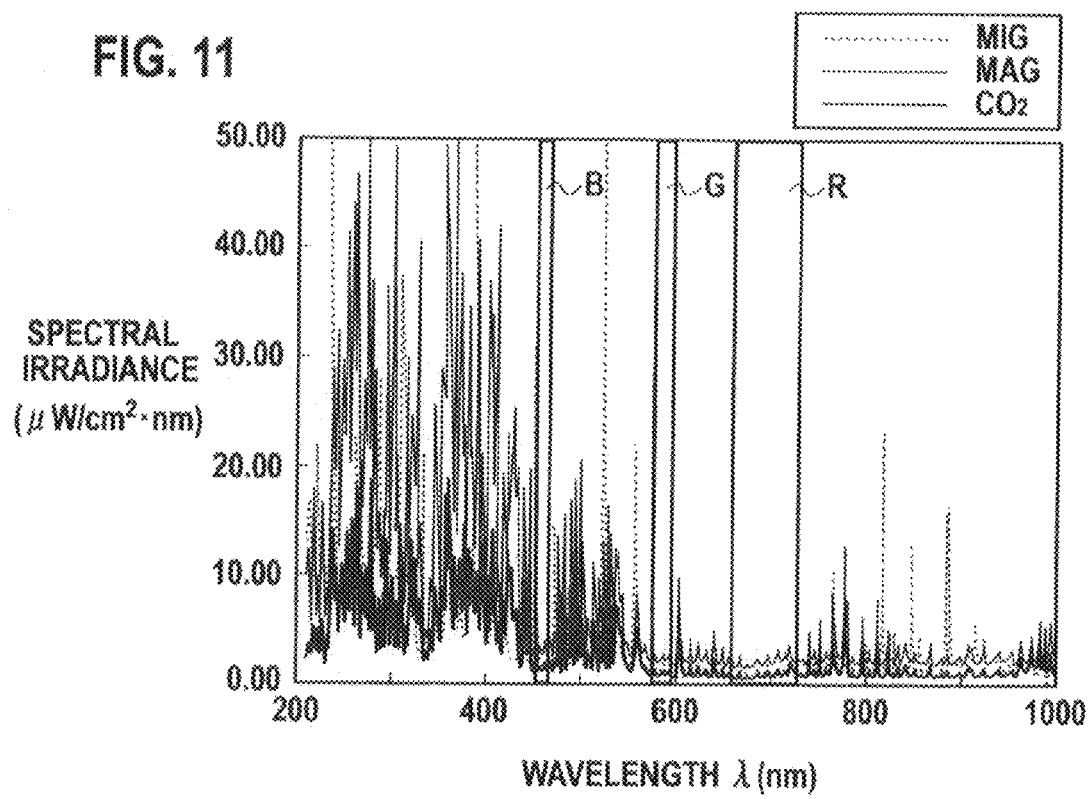
FIG. 11 It is a drawing for explaining the relation (luminescence spectrum) between the spectral irradiance and a wavelength of MIG welding, MAG welding, and $CO_2$ welding, and the existence of an optical window region of a color filter.
Figure 12:
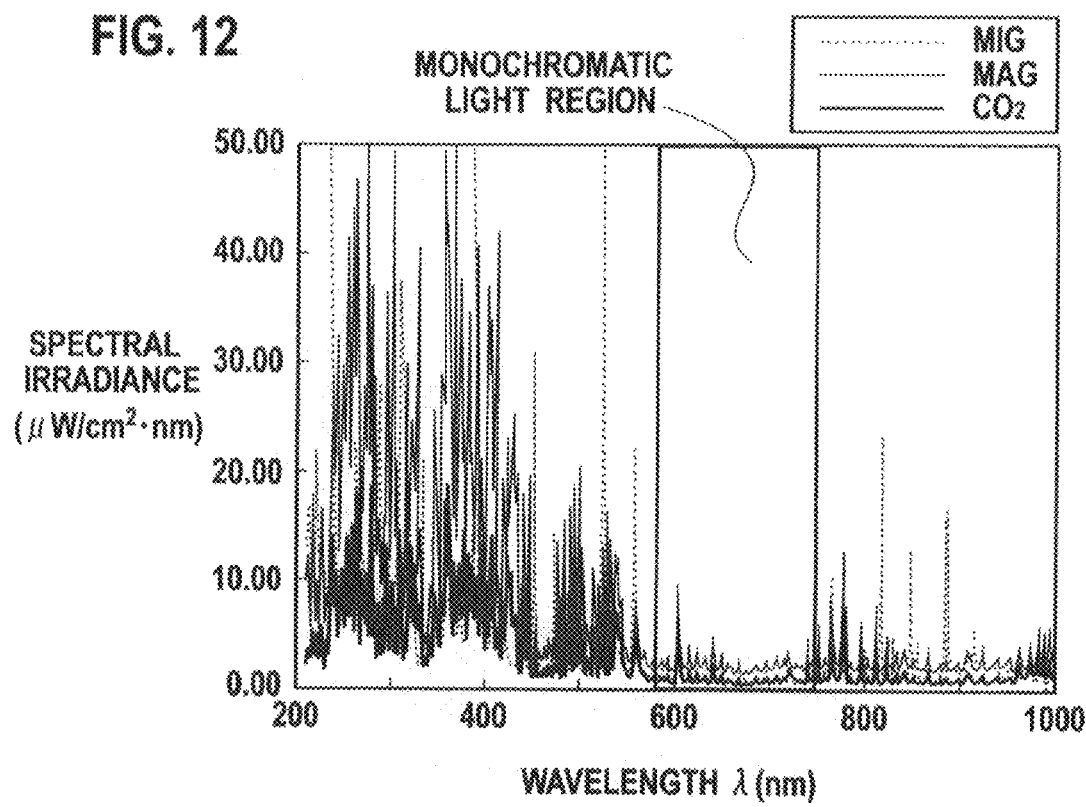
FIG. 12 It is a drawing for explaining the relation (luminescence spectrum) between the spectral irradiance and a wavelength of MIG welding, MAG welding, and $CO_2$ welding, and the existence of an optical window region of monochromatic light.

FIG. 11 is a drawing for explaining the relation (luminescence spectrum) between the spectral irradiance and the wavelength of the MIG welding, the MAG welding, and the $CO_2$ welding, and the existence of the optical window region of the color filter. FIG. 12 is a drawing for explaining the relation (luminescence spectrum) between the spectral irradiance and the wavelength of the MIG welding, the MAG welding, and the $CO_2$ welding, and the existence of the optical window region of monochromatic light.

Figure 13:
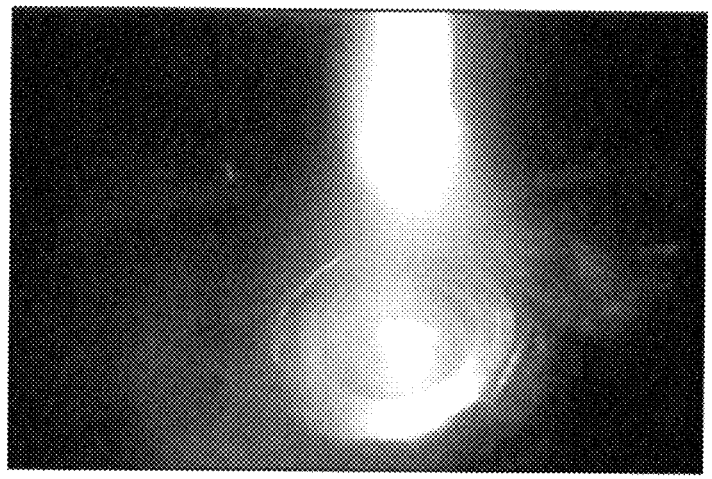
FIG. 13 It is a chart of taking a photograph at the time of arc welding observed by using the welding observation apparatus according to the first embodiment of the present invention.
Figure 14:
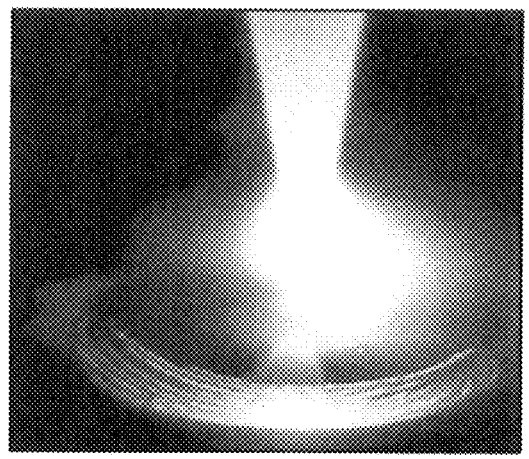
FIG. 14 It is a chart of taking a photograph at the time of another arc welding observed by using the welding observation apparatus according to the first embodiment of the present invention.

Moreover, FIG. 13 shows an example of taking a photograph at the time of arc welding observed by using the welding observation apparatus according to the first embodiment of the present invention, and FIG. 14 shows an example of taking a photograph at the time of another arc welding observed by using the welding observation apparatus according to the first embodiment of the present invention.

Figure 15:
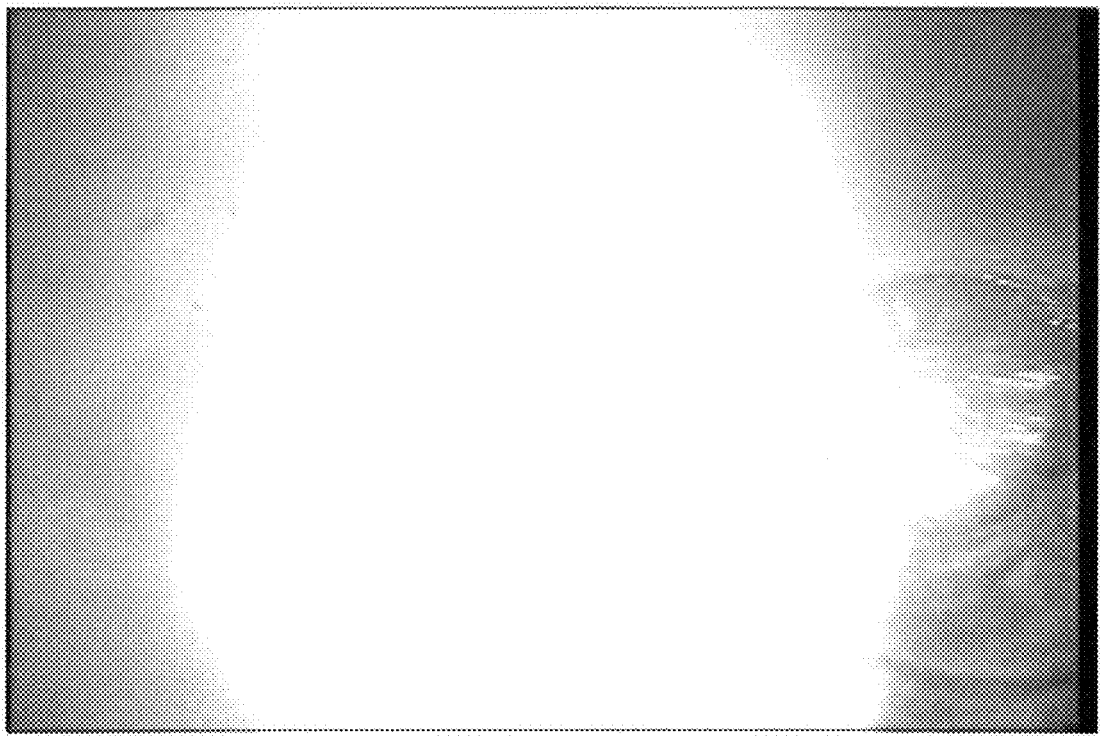
FIG. 15 It is an enlarged drawing of a high luminance part at the time of arc welding observed by using the welding observation apparatus according to the first embodiment of the present invention.

Furthermore, FIG. 15 is an enlarged drawing of a high luminance part at the time of arc welding observed by using the welding observation apparatus according to the first embodiment of the present invention.

Modified Example of First Embodiment

Figure 16:
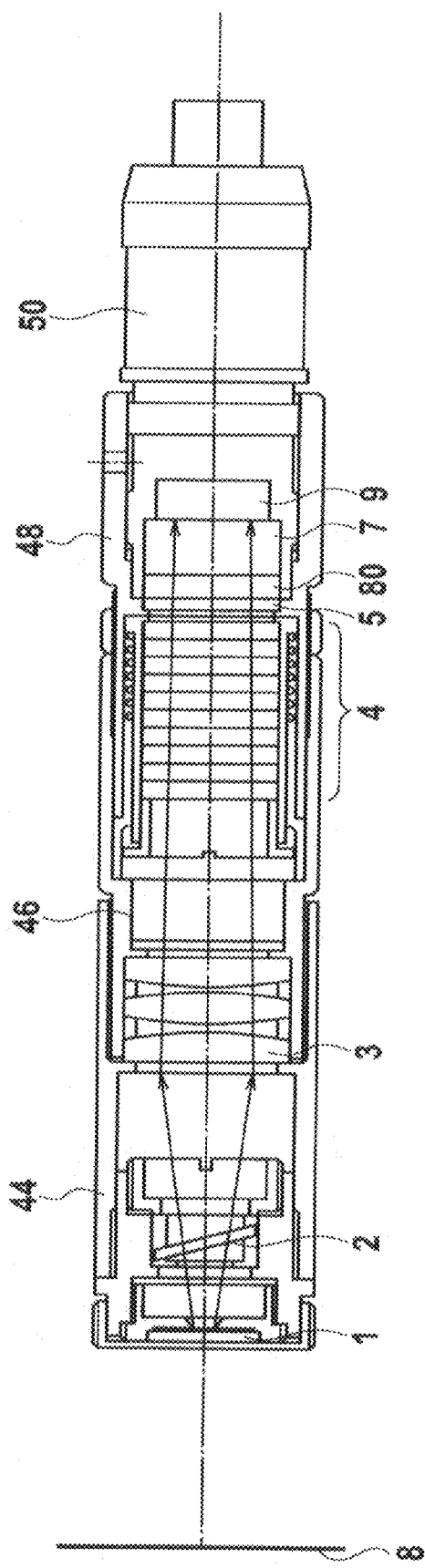
FIG. 16 It is a schematic cross-sectional configuration chart of a welding observation apparatus according to a modified example of the first embodiment of the present invention.

FIG. 16 shows a schematic cross-section structure of a welding observation apparatus according to a modified example of the first embodiment of the present invention. For example, when observing high power light, pulsed light, etc. in the welding of MIG, MAG, etc., it is available to combine a method of optical shielding in a wavelength region when the arc light cannot be dimmed only at darkening spatial (when the dimming characteristics are insufficient).

As shown in FIG. 16, the welding observation apparatus according to the modified example of the first embodiment of the present invention includes: an arc welding unit 8; an objective optical system including a the window unit 1 for concentrating the light from the arc welding unit 8, and a first colour filter 2 for illuminating with the light concentrated by the window unit 1; a telecentric optical system (3) for guiding the light passing through the first colour filter 2; a PCF 4 for illuminating with the light guided by the telecentric optical system (3); second and third colour filters (5, 80) for illuminating with the light passing through the PCF 4; and a solid state imaging device 9 for receiving the light passing through the second and third colour filters (5, 80). The light from the arc welding unit 8 is partial-darkened by the third colour filter 80 and the PCF 4.

The difference with the welding observation apparatus according to the first embodiment of the present invention shown in FIG. 1 is that the characteristics of the third colour filter 80 differ.

The welding observation apparatus according to the modified example of the first embodiment of the present invention can also be colorized by using a three-wavelength color filter of RGB as the third colour filter.

Moreover, the welding observation apparatus according to the modified example of the first embodiment of the present invention can also be colorized by using a narrow band RGB band pass filter corresponding to the optical window wavelength of the luminescence spectrum of arc welding, as the third colour filter.

Moreover, the welding observation apparatus according to the modified example of the first embodiment of the present invention can also be dimmed by performing monochromatization using a band pass filter corresponding to the optical window wavelength of the luminescence spectrum of arc welding, as the third colour filter.

That is, the welding observation apparatus according to the modified example of the first embodiment of the present invention can dim other wavelength regions with a colour filter by applying a part with little arc radiation intensity as a window, as shown by BGR in the luminescence spectrum at the time of arc welding shown in FIG. 11.

Moreover, the welding observation apparatus according to the modified example of the first embodiment of the present invention can also obtain a color image by using a filter for passing through a plurality of optical window wavelengths of BGR, in the luminescence spectrum at the time of arc welding shown in FIG. 11. In this case, it is also necessary to provide color correction means in the CCD camera side.

Moreover, the welding observation apparatus according to the modified example of the first embodiment of the present invention can observe selectively the range of 600 nm to degree 700 nm, for example, as a wavelength region by using a band pass filter, as shown in FIG. 12. The bandwidth can also be set up narrowly or can also be set up widely in the above mentioned range.

Moreover, the welding observation apparatus according to the modified example of the first embodiment of the present invention can also use the light of infrared region as another wavelength.

Moreover, the welding observation apparatus according to the modified example of the first embodiment of the present invention can also use only the colour filter, without using the PCF.

Moreover, in the welding observation apparatus according to the first embodiment of the present invention, and its modified example, the arc welding unit 8 is applicable to the TIG welding, the MIG welding, the MAG welding, or carbon dioxide gas welding.

Moreover, in the welding observation apparatus according to the first embodiment of the present invention, and its modified example, the PCF can also be provided with a modularized exchangeable structure.

Moreover, the welding observation apparatus according to the first embodiment of the present invention and its modified example is applicable to an arc welding machine.

According to the welding observation apparatus according to the first embodiment of the present invention, and its modified example, it can compose only from an optical system. Therefore, since it miniaturizes and an installing space is not necessary, space-saving is possible.

Moreover, since the welding observation apparatus according to the first embodiment of the present invention and its modified example has little number of parts, low cost is achievable.

Moreover, in the welding observation apparatus according to the first embodiment of the present invention, and its modified example, since it can be used to superimpose the PCF, it is usable enough, even if the filter performance from which the visible concentration for the amount of ultraviolet light changes is inferior or the thickness is large.

Moreover, according to the welding observation apparatus according to the first embodiment of the present invention, and its modified example, color observation is achievable.

Moreover, according to the welding observation apparatus according to the first embodiment of the present invention, and its modified example, simultaneous observation of the arc part (bright part) and the work part (dark part) is achievable.

Second Embodiment

Figure 17:
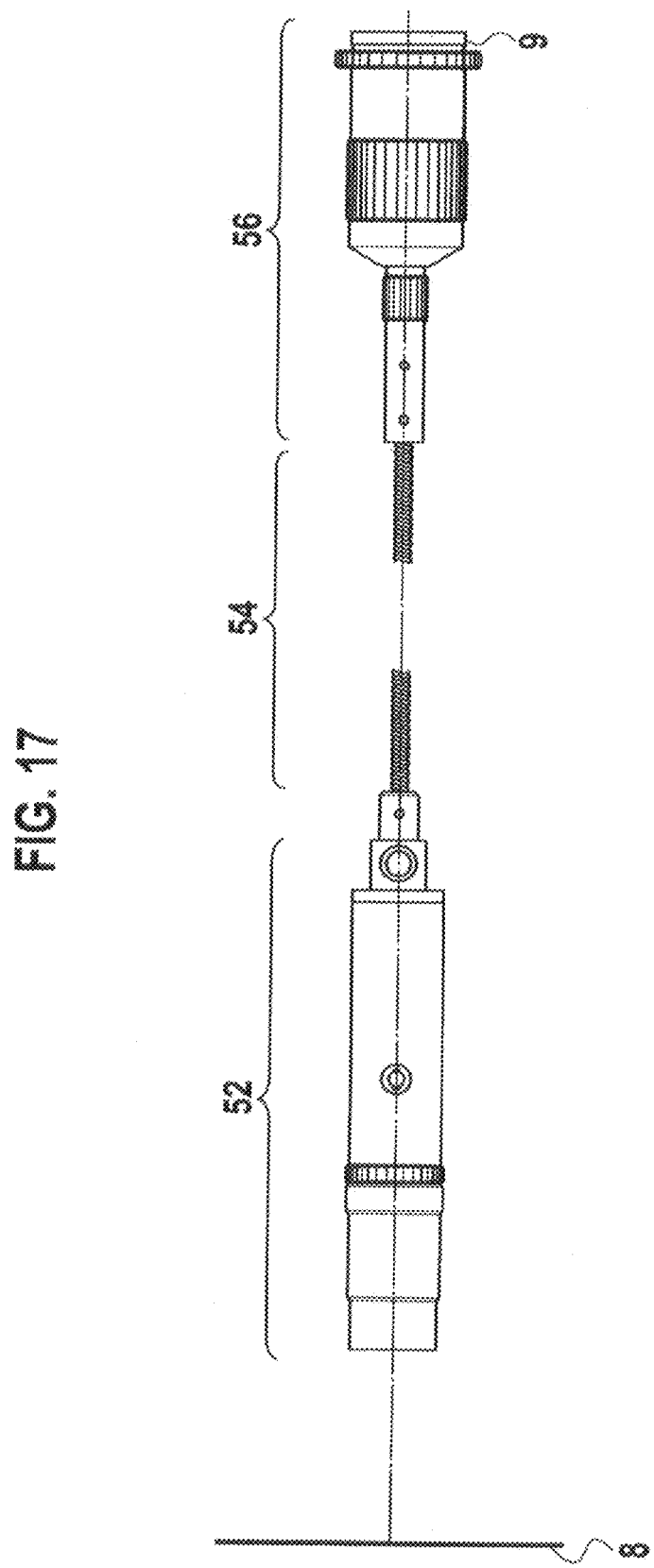
FIG. 17 It is a schematic cross-sectional configuration chart of a welding observation apparatus according to a second embodiment of the present invention.

FIG. 17 shows a schematic cross-section structure of a welding observation apparatus according to a second embodiment of the present invention. Moreover, FIG. 18 shows a whole configuration of the welding observation apparatus according to the second embodiment of the present invention.

Figure 18:
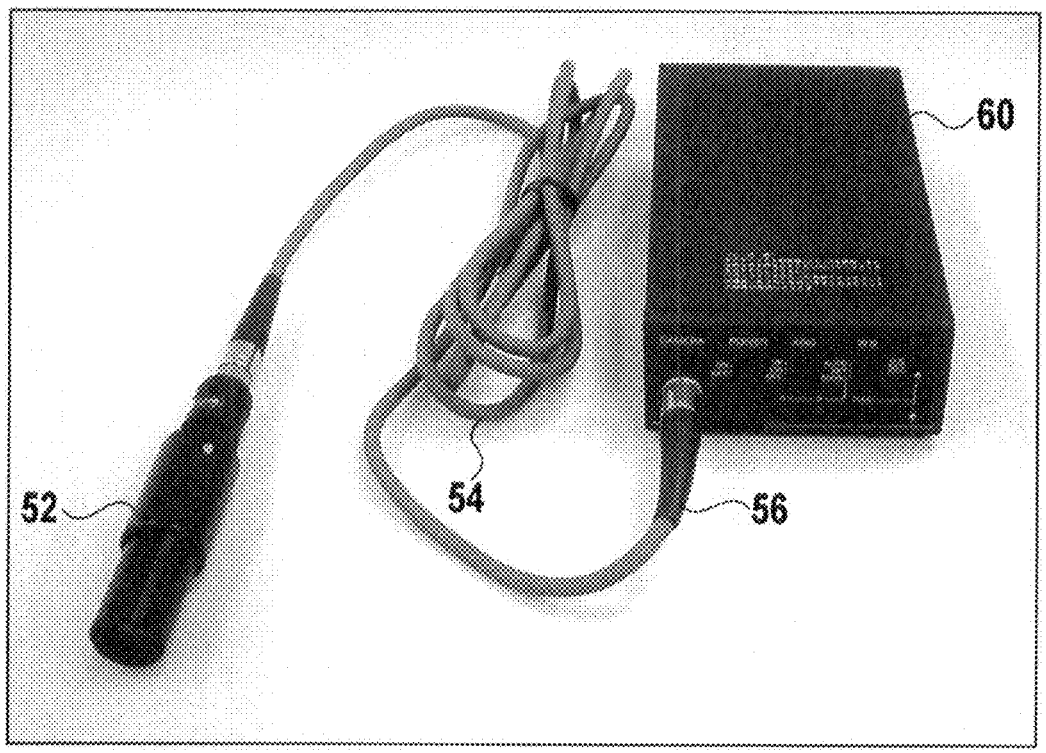
FIG. 18 It is a whole configuration chart of the welding observation apparatus according to the second embodiment of the present invention.

As shown in FIG. 18, the whole configuration of the welding observation apparatus according to the second embodiment of the present invention includes an objective optical system 52, an image fiber 54 connected to the objective optical system 52, a camera unit 56 connected to the image fiber 54, and a camera control unit 60 connected to the camera unit 56.

The welding observation apparatus according to the second embodiment of the present invention has a configuration which replaces the telecentric optical system (3) in the first embodiment by an image fiber 54, and other configurations are the same as that of the welding observation apparatus according to the first embodiment. Accordingly, the duplicating explanation are omitted about the configurations with detailed each part.

As shown in FIG. 17, the welding observation apparatus according to the second embodiment of the present invention includes: an arc welding unit 8; an objective optical system 52 for concentrating the light from the arc welding unit 8; an image fiber 54 for guiding the light concentrated by the objective optical system 52; and a camera unit 56 including a PCF 4 for illuminating with the light guided by the image fiber 54, and a solid state imaging device 9 for receiving the light passing through the PCF 4. The light from the arc welding unit 8 is partial-darkened by the PCF 4.

Alternatively, the welding observation apparatus according to the second embodiment of the present invention includes: an arc welding unit 8; an objective optical system 52 including a window unit 1 for concentrating the light from the arc welding unit 8, and a first colour filter 2 for illuminating with the light concentrated by the window unit 1; an image fiber 54 for guiding the light passing through the first colour filter 2; and the camera unit 56 including second and third colour filters (5, 6) for illuminating with the light guided by the image fiber 54, and a solid state imaging device 9 for receiving the light passing through the second and third colour filters (5, 6). The light from the arc welding unit 8 is partial-darkened by the third colour filter 6.

Alternatively, the welding observation apparatus according to the second embodiment of the present invention includes: an arc welding unit 8; an objective optical system 52 including a window unit 1 for concentrating the light from the arc welding unit 8, and a first colour filter 2 for illuminating with the light concentrated by the window unit 1; an image fiber 54 for guiding the light passing through the first colour filter 2; and a camera unit 56 including a PCF 4 for illuminating with the light guided by the image fiber 54, second and third colour filters (5, 6) for illuminating with the light passing through the PCF 4, and a solid state imaging device 9 for receiving the light passing through the second and third colour filters. The light from the arc welding unit 8 is partial-darkened by the third colour filter 6 and the PCF 4.

Moreover, the welding observation apparatus according to the second embodiment of the present invention can also be colorized by using the three-wavelength color filter of RGB as the third colour filter.

Moreover, the welding observation apparatus according to the second embodiment of the present invention can also be colorized by using a narrow band RGB band pass filter corresponding to the optical window wavelength of the luminescence spectrum of arc welding, as the third colour filter.

Moreover, the welding observation apparatus according to the second embodiment of the present invention can also be dimmed by performing monochromatization using a band pass filter corresponding to the optical window wavelength of the luminescence spectrum of arc welding, as the third colour filter.

Moreover, the welding observation apparatus according to the second embodiment of the present invention can also observe infrared light by using an infrared light band pass filter, as the third colour filter.

The welding observation apparatus according to the second embodiment of the present invention is applicable to the TIG welding, the MIG welding, the MAG welding, or carbon dioxide gas welding.

Moreover, in the welding observation apparatus according to the second embodiment of the present invention, the PCF 4 can also be provided with a modularized exchangeable structure.

Moreover, the welding observation apparatus according to the second embodiment of the present invention is applicable to an arc welding machine.

The welding observation apparatus according to the second embodiment of the present invention can intercept heat conduction to an electronic apparatus (camera unit), and can be applicable when attachment of a cooling jacket is difficult. As the heatresistant temperature, it is about 150 degrees C., for example.

A silica-based image fiber can be applied to the image fiber 54, and it is about 30,000 pixels as a pixel number, for example.

According to the welding observation apparatus according to the second embodiment of the present invention, it can compose only from an optical system. Therefore, since it miniaturizes and an installing space is not necessary, space-saving is possible.

Moreover, since the welding observation apparatus according to the second embodiment of the present invention has little number of parts, low cost is achievable.

Moreover, in the welding observation apparatus according to the second embodiment of the present invention, since it can be used to superimpose the PCF, it is usable enough even if the filter performance from which the visible concentration for the amount of ultraviolet light changes is inferior or the thickness is large.

Moreover, according to the welding observation apparatus according to the second embodiment of the present invention, color observation is achievable.

Moreover, according to the welding observation apparatus according to the second embodiment of the present invention, simultaneous observation of the arc part (bright part) and the work part (dark part) is achievable.

Other Embodiments

The present invention has been described by the first to second embodiments mentioned above, as a disclosure including associated description and drawings to be construed as illustrative, not restrictive. With the disclosure, artisan might easily think up alternative embodiments, embodiment examples, or application techniques.

The solid state imaging device for applying to the welding observation apparatus according to the first to second embodiments of the present invention is not limited to the CCD, but also applying an image sensor of other methods, such as a CMOS image sensor, an amorphous image sensor, and a MOS type image sensor.

Such being the case, the present invention covers a variety of embodiments, whether described or not. Therefore, the technical scope of the present invention is appointed only by the invention specific matter related appropriate scope of claims from the above-mentioned explanation.

Since the welding observation apparatus according to the embodiments of the present invention has the characteristic in the optical system for filtering the light emission from arc discharge in order to verify the welding condition and the monitoring of welding condition can be satisfactory under the welding arc discharge, it is suitable for incorporating to a welding supervisory apparatus in the MIG, the MAG, and the $CO_2$ welding, and an automatic welding machine, etc. Furthermore, the welding observation apparatus according to the embodiments of the present invention is applicable also as an observation apparatus of arc lamps (Xe, metal halide, etc.), a fiber fusion machine, and an apparatus using plasma. Furthermore, the welding observation apparatus according to the embodiments of the present invention is applicable also as a control apparatus of welding apparatus, and an inspection apparatus of weld.

According to the welding observation apparatus of the present invention, the monitoring of welding condition can be satisfactory by having the optical system for filtering the light emission from arc discharge in order to verify the welding condition under the welding arc discharge.

The invention claimed is:

1. A welding observation apparatus comprising:
an arc welding unit;
an objective optical system for concentrating light from the arc welding unit;
a telecentric optical system for guiding the light concentrated by the objective optical system;
a plurality of photochromic filters for illuminating with the light guided by the telecentric optical system, the photochromic filters being superimposed along a light axis; and
a solid state imaging device for receiving the light passing through the photochromic filters, the solid state imaging device being disposed adjacent the photochromic filters, wherein
a light ray flux of an ultra-violet light and a visible light adjacent the solid state imaging device is substantially parallel each other,
the telecentric optical system guides the light so that an ultra-violet image is not made to form an image on any one of the photochromic filters, and that the light ray flux of the ultra-violet light and the visible light does not spread in a whole area of each of the photochromic filters, but is passed through said each of the photochromic filters on a small scale partially, and
the light from the arc welding unit is partial-darkened by the photochromic filters.

2. The welding observation apparatus according to claim 1, wherein
the arc welding unit is formed by TIG welding.

3. The welding observation apparatus according to claim 1, wherein
the arc welding unit is formed by MIG welding.

4. The welding observation apparatus according to claim 1, wherein
the arc welding unit is formed by MAG welding.

5. The welding observation apparatus according to claim 1, wherein
the arc welding unit is formed by carbon dioxide gas welding.

6. The welding observation apparatus according to claim 1, wherein
the photochromic filter is provided with a modularized exchangeable structure.

7. An arc welding machine comprising the welding observation apparatus according to claim 1.

8. A welding observation apparatus comprising:
an arc welding unit;
an objective optical system including a window unit for concentrating light from the arc welding unit, and a first colour filter for illuminating with the light concentrated by the window unit;

a telecentric optical system for guiding the light passing through the first colour filter;

a plurality of photochromic filters for illuminating with the light guided by the telecentric optical system, the photochromic filters being superimposed along a light axis;

second and third colour filters for illuminating with the light passing through the photochromic filters; and a solid state imaging device for receiving the light passing through the second and third colour filters, the solid state imaging device being disposed adjacent the second and third colour filters, wherein a light ray flux of an ultra-violet light and a visible light adjacent the solid state imaging device is substantially parallel each other, the telecentric optical system guides the light so that an ultra-violet image is not made to form an image on any one of the photochromic filters, and that the light ray flux of the ultra-violet light and the visible light does not spread in a whole area of each of the photochromic filters, but is passed through said each of the photochromic filters on a small scale partially, and the light from the arc welding unit is partial-darkened by the third colour filter and the photochromic filters.

9. A welding observation apparatus comprising, an arc welding unit;

an objective optical system including a window unit for concentrating light from the arc welding unit, and a first colour filter for illuminating with the light concentrated by the window unit;

a telecentric optical system for guiding the light passing through the first colour filter;

second and third colour filters for illuminating with the light guided by the telecentric optical system; and a solid state imaging device for receiving the light passing through the second and third colour filters, wherein the light from the arc welding unit is partial-darkened by the third colour filter, and the welding observation apparatus is colorized by using a three-wavelength color filter of RGB as the third colour filter.

10. A welding observation apparatus comprising, an arc welding unit;

an objective optical system including a window unit for concentrating light from the arc welding unit, and a first colour filter for illuminating with the light concentrated by the window unit;

a telecentric optical system for guiding the light passing through the first colour filter;

second and third colour filters for illuminating with the light guided by the telecentric optical system; and a solid state imaging device for receiving the light passing through the second and third colour filters, wherein the light from the arc welding unit is partial-darkened by the third colour filter, and the welding observation apparatus is colorized by using a narrow band RGB band pass filter corresponding to an optical window wavelength of luminescence spectrum of the arc welding as the third colour filter.

11. A welding observation apparatus comprising, an arc welding unit;

an objective optical system including a window unit for concentrating light from the arc welding unit, and a first colour filter for illuminating with the light concentrated by the window unit;

a telecentric optical system for guiding the light passing through the first colour filter, second and third colour filters for illuminating with the light guided by the telecentric optical system; and a solid state imaging device for receiving the light passing through the second and third colour filters, wherein the light from the arc welding unit is partial-darkened by the third colour filter, and the welding observation apparatus is dimmed by performing monochromatization using a band pass filter corresponding to an optical window wavelength of luminescence spectrum of the arc welding as the third colour filter.

12. A welding observation apparatus comprising, an arc welding unit;

an objective optical system including a window unit for concentrating light from the arc welding unit, and a first colour filter for illuminating the light concentrated by the window unit;

a telecentric optical system for guiding the light passing through the first colour filter, second and third colour filters for illuminating with the light guided by the telecentric optical system; and a solid state imaging device for receiving the light passing through the second and third colour filters, wherein the light from the arc welding unit is partial-darkened by the third colour filter, and infrared light is observed by using an infrared light band pass filter as the third colour filter.

13. A welding observation apparatus comprising:

an arc welding unit;

an objective optical system including a window unit for concentrating light from the arc welding unit, and a first colour filter for illuminating with the light concentrated by the window unit;

an image fiber for guiding the light passing through the first colour filter;

a camera unit including second and third colour filters for illuminating with the light guided by the image fiber, and a solid state imaging device for receiving the light passing through the second and third colour filters, wherein the light from the arc welding unit is partial-darkened by the third colour filter.

14. The welding observation apparatus according to claim 13, wherein the welding observation apparatus is colorized by using a three-wavelength color filter of RGB as the third colour filter.

15. The welding observation apparatus according to claim 13, wherein the welding observation apparatus is colorized by using a narrow band RGB band pass filter corresponding to an optical window wavelength of luminescence spectrum of the arc welding as the third colour filter.

16. The welding observation apparatus according to claim 13, wherein the welding observation apparatus is dimmed by performing monochromatization using a band pass filter corresponding to an optical window wavelength of luminescence spectrum of the arc welding as the third colour filter.

17. The welding observation apparatus according to claim 13, wherein infrared light is observed by using an infrared light band pass filter as the third colour filter.

18. A welding observation apparatus comprising:

an arc welding unit;

an objective optical system including a window unit for concentrating light from the arc welding unit, and a first colour filter for illuminating with the light concentrated by the window unit;

an image fiber for guiding the light passing through the first colour filter; and a camera unit including a photochromic filter for illuminating with the light guided by the image fiber, second and third colour filters for illuminating with the light passing through the photochromic filter, and a solid state imaging device for receiving the light passing through the second and third colour filters, wherein the light from the arc welding unit is partial-darkened by the third colour filter and the photochromic filter.

* * * * *